(12) United States Patent
Huang et al.

(10) Patent No.: US 10,918,312 B2
(45) Date of Patent: Feb. 16, 2021

(54) WEARABLE AND CONNECTED GAIT ANALYTICS SYSTEM

(71) Applicants: Case Western Reserve University, Cleveland, OH (US); THE RESEARCH FOUNDATION FOR STATE UNIVERSITY OF NEW YORK, Buffalo, NY (US)

(72) Inventors: Ming-Chun Huang, Cleveland, OH (US); Wenyao Xu, Buffalo, NY (US)

(73) Assignees: CASE WESTERN RESERVE UNIVERSITY, Cleveland, OH (US); THE RESEARCH FOUNDATION FOR STATE UNIVERSITY OF NEW YORK, Buffalo, NY (US)

( * ) Notice: Subject to any disclaimer, the term of this patent is extended or adjusted under 35 U.S.C. 154(b) by 294 days.

(21) Appl. No.: 15/764,084

(22) PCT Filed: Sep. 28, 2016

(86) PCT No.: PCT/US2016/054177
§ 371 (c)(1),
(2) Date: Mar. 28, 2018

(87) PCT Pub. No.: WO2017/058913
PCT Pub. Date: Apr. 6, 2017

(65) Prior Publication Data
US 2018/0279915 A1 Oct. 4, 2018

Related U.S. Application Data

(60) Provisional application No. 62/233,832, filed on Sep. 28, 2015.

(51) Int. Cl.
*A61B 5/00* (2006.01)
*A61B 5/11* (2006.01)
(Continued)

(52) U.S. Cl.
CPC .............. *A61B 5/112* (2013.01); *A61B 5/002* (2013.01); *A61B 5/1038* (2013.01);
(Continued)

(58) Field of Classification Search
CPC ......... A61B 5/11; A61B 5/112; A61B 5/1116; A61B 5/1117; A61B 5/002; A61B 5/1038;
(Continued)

(56) References Cited

U.S. PATENT DOCUMENTS 8,823,526 B2   9/2014  Kaiser et al.
8,990,041 B2 *  3/2015  Grabiner ............... A61B 5/1116
                                              702/141

(Continued)

OTHER PUBLICATIONS

Extended European Search report dated Aug. 19, 2019.
Supplemental European Search report dated Sep. 5, 2019.
Partial European Search report dated Feb. 7, 2019.

*Primary Examiner* — Max F Hindenburg
(74) *Attorney, Agent, or Firm* — Tarolli, Sundheim, Covell & Tummino LLP (57) ABSTRACT

This disclosure relates to systems and methods to analyze gait, balance or posture information extracted from data collected by one or more wearable and connected sensor devices with sensors embedded therewithin. The embedded sensors include a three-axis accelerometer, a three-axis gyroscope and an array of pressure sensors. Sensor data detected by the sensors can be received by a mobile computing device, which can analyze the sensor data to identify a pattern related to gait, balance or posture within the sensor data; and apply a statistical/machine learning-based classification to the pattern related to gait, balance or posture to assign a clinical parameter to the pattern characterizing a risk of a slip, trip and fall event.

16 Claims, 5 Drawing Sheets

(51) Int. Cl.
*A61B 5/103* (2006.01)
*G01P 15/18* (2013.01)
*G01R 33/02* (2006.01)

(52) U.S. Cl.
CPC .......... *A61B 5/1116* (2013.01); *A61B 5/1117* (2013.01); *A61B 5/4023* (2013.01); *A61B 5/6807* (2013.01); *A61B 5/7264* (2013.01); *A61B 5/746* (2013.01); *A61B 5/7455* (2013.01); *A61B 5/7267* (2013.01); *A61B 5/7275* (2013.01); *A61B 2562/0219* (2013.01); *A61B 2562/0223* (2013.01); *A61B 2562/0247* (2013.01); *G01P 15/18* (2013.01); *G01R 33/0206* (2013.01)

(58) Field of Classification Search
CPC ..... A61B 5/7264; A61B 5/746; A61B 5/6807; A61B 5/7445; A61B 5/4023
See application file for complete search history.

(56) References Cited

U.S. PATENT DOCUMENTS

| | | |
|---|---|---|
| 9,489,815 B2 * | 11/2016 | Ten Kate .............. A61B 5/1116 |
| 9,801,568 B2 | 10/2017 | Ziaie et al. |
| 2012/0083237 A1 | 4/2012 | Fish et al. |
| 2012/0253233 A1 | 10/2012 | Greene et al. |
| 2014/0276130 A1 | 9/2014 | Mirelman et al. |
| 2015/0157274 A1 | 6/2015 | Ghassemzadeh et al. |

* cited by examiner

WEARABLE AND CONNECTED GAIT ANALYTICS SYSTEM

RELATED APPLICATIONS

This application claims the benefit of U.S. Provisional Application No. 62/233,832, filed Sep. 28, 2015, entitled "Portable Gait Lab: Preventing Work-Related Injuries in Construction, Wholesale and Retail Trade Workspaces Using Wearable Computer Technology." The entirety of this provisional application is hereby incorporated by reference in its entirety for all purposes.

TECHNICAL FIELD

This disclosure generally relates to a wearable and connected gait analytics system and, more specifically, to systems and methods to analyze gait, balance or posture information extracted from data collected by one or more wearable devices.

BACKGROUND

Properties of locomotion, including gate, balance and posture, each depend on the coordination and support from several body systems, including one or more of the visual system, the auditory system, the vestibular system, the motor system, the sensory system and other higher level premotor systems. Disorders of one or more properties of locomotion can be found most commonly in the elderly; however, such disorders are also seen in a smaller number of children. Traditionally, to evaluate these properties of locomotion, subjects have been required to undergo tests in a clinical gait lab setting. However, the clinical gait lab may not be accessible to all subjects. Additionally, these tests, lack mobility and portability, which may lead to environmental bias concerns and cannot reflect the subject's natural behaviors.

SUMMARY

According to an aspect, a non-transitory computer readable medium is described. The non-transitory computer readable medium can comprise computer executable instructions that when executed by a processing resource facilitate the performance of operations. The operations include: receiving sensor data from sensors embedded within a wearable device; analyzing the sensor data to identify a pattern related to gait, balance or posture within the sensor data; and applying a statistical or machine learning-based classification to the pattern related to gait, balance or posture to assign a clinical parameter to the pattern characterizing a risk of a slip, trip and fall (STF) event. The sensors include a three-axis accelerometer, a three-axis gyroscope and an array of pressure sensors embedded within the wearable device.

According to another aspect, a system is described. The system can include a wearable device and a portable computing device communicating according to a short range communication protocol. The wearable device includes a plurality of sensors to detect data; a power management unit to set a sampling rate for the plurality of sensors; and a data exchange unit to stream a signal comprising the data to a portable computing device according to the short range communication protocol and to receive data from the portable computing device. The portable computing device includes: a communications unit to receive the signal streamed according to the short range communication protocol; a non-transitory memory storing machine readable instructions; and a processor to execute the machine readable instructions. Upon execution, the machine readable instructions cause the portable computing device to: analyze the data to identify a pattern related to gait, balance or posture within the data; and apply a statistical or machine learning-based classification to the pattern related to gait, balance or posture to assign a clinical parameter to the pattern.

According to a further aspect, a method is described. At least a portion of the acts of the method can be performed by a system comprising a processor (e.g., a processing core, a processing unit or the like). The method includes receiving a signal comprising sensor data from sensors according to a short range communication protocol. The sensors include a three-axis accelerometer, a three-axis gyroscope and an array of pressure sensors embedded within a wearable device. The sensor data can be analyzed to identify a pattern related to gait, balance or posture within the quantized data. A statistical or machine learning-based classification can be applied to the pattern related to gait, balance or posture to assign a clinical parameter to the pattern. A risk of a slip, trip and fall (STF) event can be determined based on the clinical parameter satisfying a STF condition.

DETAILED DESCRIPTION

This disclosure generally relates to a wireless portable gait system that includes a wearable device in wireless communication with a mobile computing device. The wireless communication distinguishes the wireless portable gait system from traditional clinical gait labs. Clinical gait labs have a subject perform tests in a laboratory setting using equipment that is wired for data transfer. The clinical gait labs are confined to a laboratory setting and, therefore, not wearable or user friendly. Additionally, the laboratory setting leads to environmental bias since the laboratory is not the subject's natural environment and the tests are not natural behavior. The wireless portable gait system allows for user friendly, accurate and ubiquitous testing related to gait, balance or posture in real time. The wireless portable gait system allows the testing to be conducted in the subject's natural environment, so that the results reflect the subject's natural behavior, eliminating environmental bias concerns.

The wearable device can provide a portable, user friendly solution for detecting data related to a subject's gait, balance or posture in the subject's natural environment. As an example, the wearable device can be one or more shoe insoles embedded with sensors that can be configured to capture data indicative of movement. As another example, the wearable device can be one or more shoes. The wearable device can send the data related to the subject's gate wirelessly to the mobile computing device for analysis. The portable computing device can analyze the data to determine identify any unstable pattern and apply a statistical or machine learning-based classification to assign one or more clinical parameters to the unstable pattern. The term "clinical parameter" is used herein to refer to one or more clinical parameters.

The clinical parameter can be used to provide personalized healthcare related to gait, balance or posture to a subject. As an example, the clinical parameter can be used to detect, quantify or characterize a risk of a slip, trip and fall (STF) event. STF events are common among patients with neurological disorders, like Parkinson's disease. However, STF events are also common in generally healthy people in the workplace (e.g., especially common in the construction industry or retail trades). The wireless portable gait system can be used to provide real-time and continuous sensory surveillance, risk identification and just-in-time intervention methods related to a STF event that occur before the STF event happens, significantly enhancing the subject's safety and health.

Figure 1:
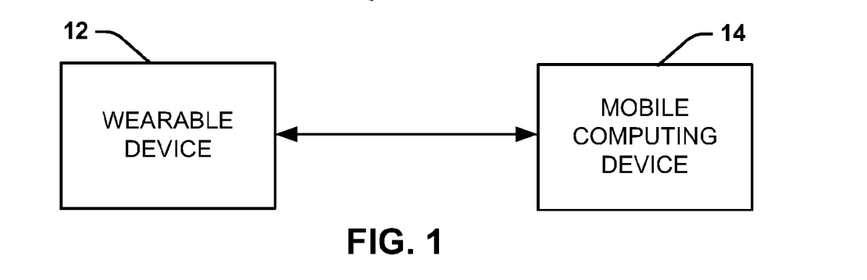
FIG. 1 illustrates an example of a wireless portable gait system.

FIG. 1 illustrates a wireless portable gait system 10 that includes a wearable device 12 configured for wireless communication with a mobile computing device 14. The wearable device 12 includes sensors to collect data related to gait, balance or posture. The wearable device 12 sends the data to the mobile computing device 14 according to a wireless communication protocol. The mobile computing device 14 analyzes gait, balance or posture information extracted from data collected by the wearable device 12. In some examples, the wireless communication can be unilateral from the wearable device 12 to the mobile computing device 14. In other examples, the wireless communication can be bidirectional between the wearable device 12 and the mobile computing device 14. The wireless communication protocol can be a short-range communication protocol, such as Bluetooth, Bluetooth Low Energy (BLE), WiFi, ZigBee or the like.

Figure 2:
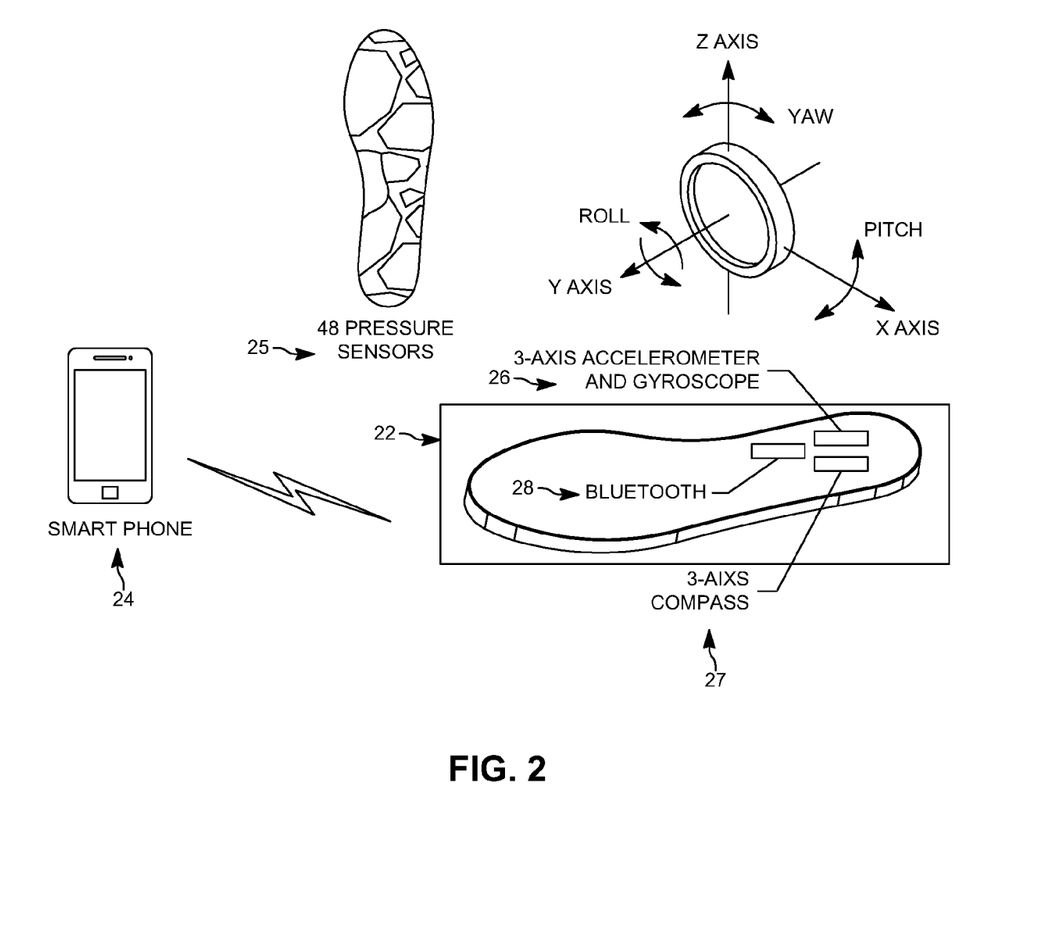
FIG. 2 illustrates an example of implementation of the wireless portable gait system in FIG. 1.

FIG. 2 illustrates an example implementation of the system 10. In FIG. 2, the wearable device 12 is implemented as an insert 22 for a shoe. The example of the insert 22 illustrated in FIG. 2 can be an insole. However, the wearable device 12 can be other devices other than the insert 22. In one example, the wearable device 12 can be an entire shoe. In another example, the wearable device 12 can be a portion of the shoe, such as the bottom.

The insert 22 includes a plurality of sensors embedded therein, which provide reliable and accurate detection of gait, balance or posture data and enhance the user-experience compared to a traditional clinical gait lab. The mobile computing device 14 is implemented as a smartphone 24. However, the mobile computing device 14 can be implemented as a tablet, a laptop or the like. The insert 22 and the smartphone 24 can communicate bidirectionally according to a Bluetooth 26 communication protocol. In some examples, a subject can wear one or more inserts 22 (e.g., an insert 22 in each shoe) to facilitate testing of gait, balance or posture. The terms "subject", "patient" and "user" can be used interchangeably herein to refer to a bipedal animal, like a human.

Figure 3:
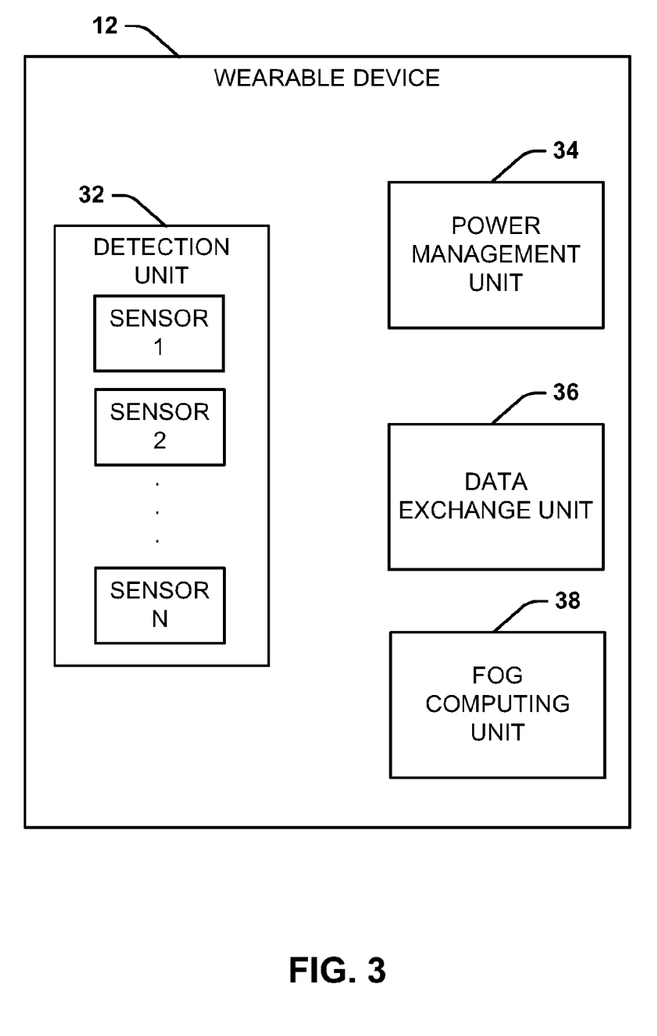
FIG. 3 illustrates an example configuration of the wearable device in FIG. 1.

FIG. 3 illustrates an example of the wearable device 12 of FIG. 1. The wearable device 12 can include a detection unit 32, a power management unit 34 and a data exchange unit 36. The detection unit 32 can include a plurality of individual sensors (e.g., sensor 1-N, where N is an integer value of 2 or greater). As an example, the individual sensors can be analog sensors, implemented on one or more flexible circuit boards, to detect data based on the specific type of sensor. The detection unit 32 can also include sensors that are outside the wearable device 12. For example, the sensors outside the wearable device can include EMG sensors that sense activity in the calf muscle or other muscles of the leg.

In the example shown in FIG. 2, the sensors can include a pressure sensor array (e.g., an array of 48 pressure sensors that can provide a pressure map 25), three-axis inertial sensors (e.g., a three-axis accelerometer and gyroscope 26), and a three-axis sensor used for calibrating the inertial sensors (e.g., a three-axis compass 27). The array of pressure sensors can substantially homogeneously cover the surface of the insert 22. While the insert 22 of FIG. 2 is shown as containing 48 pressure sensors, the array of pressure sensors can be arranged with any number of pressure sensors greater than two. In some examples, the pressure sensor array can have twelve or more pressure sensors. In other examples, the pressure sensor array can have 64 of more pressure sensors. The pressure sensor array, as an example, can be based on an advanced fabric sensor technique that can be integrated into the wearable device 12 of FIG. 1.

The three-axis accelerometer and three-axis gyroscope are inertial sensors, which can measure motion. The three-axis magnetometer can be used as a baseline when the inertial sensors are calibrated. The three-axis accelerometer, three-axis gyroscope and three-axis magnetometer can each record data related to pitch, roll and yaw. The pitch corresponds to rotation about the x-axis. The roll corresponds to rotation about the y-axis. The yaw corresponds to rotation about the z-axis. Accordingly, motion can be sensed with nine degrees of freedom.

Referring again to FIG. 3, the power management unit 34 can control acquisition of the data. The acquisition can be controlled to conserve power of the wearable device 12. For example, power can be provided by a battery, which can be recharged or replaced. One way the power management unit 34 can conserve power of the wearable device 12 is by a setting a sampling rate for the data to conserve power of the battery. For example, the sampling rate can be 100 samples per second or less. As another example, the sampling rate can be 50 samples per second or less. As another example, the sampling rate can be adaptively changed based on signal reconstruction requirements of the mobile computing device 14. A subject's gait has four stages per cycle: swing, contact, midstance and propulsive. The pressure distribution of each stage is different and selected inertial measurement units and pressure sensors can be used to determine the gait phase. If there is no pressure under the foot in the swing stage, then there is no need to sample the pressure image. Accordingly, the sampling rate can be adaptively changed during the four stages in each gait cycle.

The power management unit 34 can quantize the sensor data based on the sampling rate. The power management unit 34 can include an analog-to-digital convertor, which can quantize the sensor data for transmission. As an example, the analog-to-digital convertor can be an 8-channel, 12-bit, 0-3.3 volt analog-to-digital module. However, other analog-to-digital convertor configurations can be used in the power management unit 34.

The data exchange unit 36 is configured to communicate with the mobile computing device 14 according to the wireless communication protocol. For example, the wireless communication protocol can be a short-range, low power communication protocol. The communication can be unidirectional (between the wearable device 12 and the mobile computing device 14) or bidirectional (both ways between the wearable device 12 and the mobile computing device). The data exchange unit 36 can stream a signal comprising the quantized data to the mobile computing device 14 and receive a response to the data from the mobile computing device 14. The response to the data can be, for example, an alarm trigger.

In some examples, the wearable device 12 can include a Fog computing unit 38. The Fog computing unit 38 can be an on-board machine learning unit. The use of the on-board machine learning Fog computing unit 38 can further reduce the amount of wireless data sent to the mobile computing device 14. The machine learning-based algorithm enables long-lived nodes by extracting features of interest from the sensor data streams. The resultant classified low-data-rate outputs can then be transmitted with much lower power consumption than the raw data. Moreover, the Fog computing unit 38 can also save power by monitoring ambient conditions and only waking up the power-hungry wireless transceiver when anomalous/interesting patterns occur in the data.

Figure 4:
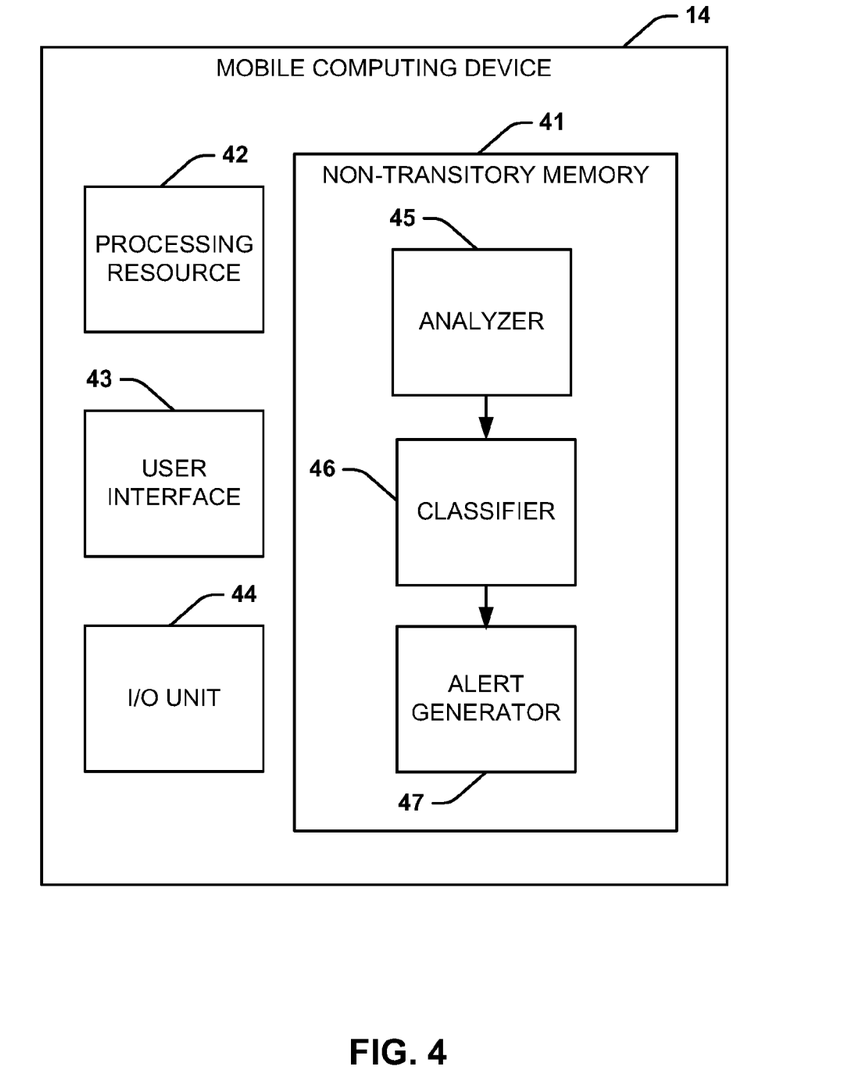
FIG. 4 illustrates an example configuration of the mobile computing device in FIG. 1.

FIG. 4 illustrates an example configuration of the mobile computing device 14 of FIG. 1. The mobile computing device 14 can include a non-transitory memory 41, a processing resource 42 (e.g., one or more processor cores), a user interface 43 and an input/output (I/O) unit 44. Although not illustrated, the mobile computing device 14 can have a system bus to facilitate communication between at least two of the non-transitory memory 41, processing resource 42, user interface 43 and I/O unit 44. The user interface 43 can display visual or audio information to the user. The user interface 43 can also receive inputs from the user. As an example, the user interface 43 can be a touchscreen that can both display visual information and receive user inputs. The I/O unit 44 can receive the signal, which includes the quantized data, streamed according to the communication protocol by the wearable device 12. Accordingly, the I/O unit 44 includes an interface to communicate with the wearable device 12 according to the wireless protocol. In some examples, the I/O unit 44 can also include another interface to communicate according to another wireless protocol (e.g., a cellular communication protocol). In still other examples, the I/O unit 44 can access a cloud data center, remote server, or a plurality of remote servers to exchange data.

The non-transitory memory 41 can store machine-readable instructions, which the processing resource 42 can execute to cause the mobile computing device 14 to perform operations of an analyzer 45 and a classifier 46. In some examples, the mobile computing device 14 can also perform the operations of an alert generator 47. For example, the non-transitory memory can be a computer-usable or computer-readable medium that can contain or store the machine-readable instructions (which are, for example, a program) for use by or in connection with the instruction or execution of a system, apparatus or device (like the mobile computing device 14) by the processing resource 42. The computer-usable or computer-readable medium can be, for example but not limited to, random access memory (RAM), flash memory, a solid state drive (SSD), a hard disk drive (HDD) or a combination thereof.

The analyzer 45 can perform analysis tasks on the data. The analysis tasks can include preprocessing tasks such as calibrating the data, synchronizing the data (e.g., ensuring that the data corresponds to the same time), fusing the data or removing noise from the data. As an example, the inertial data from the three-dimensional accelerometer and three-dimensional gyroscope can be filtered and calibrated using the three-dimensional magnetometer data. Additionally, noise can be removed from the pressure data from the pressure array. The analyzer 45 can perform additional analysis tasks on the preprocessed data, including identifying one or more unstable patterns within the data. The unstable patterns can be associated with one or more of gait, balance or posture. For example, features related to gait that may be represented by unstable patterns include walking speed, stride height, stride length, landing position, underfoot pressure, path distance, path variation, speed of leg movement, speed difference between left and right legs, foot orientation, cadence or swing time. As another example, features related to balance that may be represented by unstable patterns include the center of pressure based on one or more indices derived from a statokinesiagram (SKG), including SKG index, maximum mediolateral and anteroposterior trajectory excursions, mean mediolateral and anteroposterior trajectory excursions or the standard deviation of mediolateral and anteroposterior trajectory excursions. As a further example, unstable patterns related to body posture may be related to a pressure map constructed based on data recorded by the array of pressure sensors.

The classifier 46 can apply a statistical or machine learning-based classification to the unstable pattern related to gait, balance or posture in relation to a historical pattern to assign a clinical parameter to the pattern. The classifier 46 can be adaptable to reflect the flexible design described herein. In some examples, the classifier 46 can communicate with an external device through the I/O unit 44 to reduce the power of the mobile computing device 14 consumed during the statistical or machine learning-based classification. The external device can perform at least some of the processing related to the statistical or machine learning-based classification. However, in most examples, the classifier 46 can access historical data related to the unstable pattern identified by the analyzer. The historical data, as one example, can be previous data recorded from the subject in a clinical gait lab and used as baseline data. As another example, the historical data can be previous data recorded from a group of other subjects with similar medical histories. More specifically, the historical data applied to a subject suffering from multiple sclerosis can be based on previous data from a group of other subjects also suffering from multiple sclerosis. Similarly, the historical data applied to a healthy subject can be based on previous data from a group of healthy subjects. When used as a diagnostic device, the unstable pattern can be compared to a plurality of historical data, each from a different plurality of subjects with a different plurality of candidate conditions.

In one example, the statistical or machine learning-based classification applied by the classifier 46 can employ one or more pattern recognition classifiers, each of which utilize the extracted features or a subset of the extracted features to determine an appropriate clinical parameter. Where multiple classifiers are used, an arbitration element can be utilized to provide a coherent result from the plurality of classifiers. Each classifier is trained on a plurality of training patterns representing various classes of interest. The training process of the a given classifier will vary with its implementation, but the training generally involves a statistical aggregation of training data from a plurality of training images into one or more parameters associated with the output class. Any of a variety of optimization techniques can be utilized for the classification algorithm, including support vector machines, self-organized maps, fuzzy logic systems, data fusion processes, ensemble methods, statistical or machine learning-based systems or artificial neural networks. The outcome class can represent a particular clinical parameter for the subject. From the provided feature vector, an outcome class is selected and a confidence in the selected result can be calculated. Results falling below a threshold confidence value can be rejected.

For example, a support vector machine (SVM) classifier can process the training data to produce functions representing boundaries in a feature space defined by the various attributes of interest. Similarly, a convolutional neural network (CNN) classifier can process the training data to determine a set of interconnection weights corresponding to the interconnections between nodes in its associated the neural network. The CNN is generally a structured/multi-layer version of a neural network.

A SVM classifier can utilize a plurality of functions, referred to as hyperplanes, to conceptually divide boundaries in the M-dimensional feature space, where each of the M dimensions represents one associated feature of the feature vector. The boundaries define a range of feature values associated with each class. Accordingly, an output class and an associated confidence value can be determined for a given input feature vector according to its position in feature space relative to the boundaries. A statistical or machine learning-based classifier applies a set of logical rules to the extracted features to select an output class. Generally, the rules are applied in order, with the logical result at each step influencing the analysis at later steps.

A CNN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the CNN, with each node having an associated value representing a confidence for one of the associated output classes of the classifier.

In another example, the statistical or machine learning-based classification applied by the classifier 46 can employ a regression model configured to provide calculate a parameter representing a likelihood that the subject exhibits the clinical parameter. In yet another example, the statistical or machine learning-based classification applied by the classifier 46 can employ a sensitivity analysis using the model, such that a magnitude of the effect of one or more features on the at least one parameter can be determined and correlated to the clinical parameter.

The clinical parameter assigned by the classifier 46 can relate to a certain medical condition. In some examples, the clinical parameter can be used in the diagnosis, stratification or monitoring of a medical condition that affects the musculoskeletal system, like multiple sclerosis, Parkinson's disease, hemiplegia after stroke, traumatic brain injury, spinal cord injury, senile dementia, vestibular vertigo, cervical vertigo, vascular vertigo, osteoarthritis disease or injury, peripheral nerve injury, muscle spasm/muscle atrophy/muscle weakness, muscle pain, postoperative fractures or sprains or the like. The clinical parameter, as another example, can be used to determine, track or ensure the subject's compliance with certain exercise or rehabilitation programs. In other examples, the clinical parameter can be used for just-in-time intervention before the occurrence of an event (like syncope, falling, loss of balance, etc.). The just-in-time intervention can be used to prevent Slip, Trip and Fall (STF) events in the workplace or in a rehabilitation/exercise setting.

The alert generator 47 can be used in some examples to provide an alert based on the clinical parameter. It will be understood that the alert generator 47 is not necessary with every implementation of the mobile computing device 14. In some implementations, the clinical parameter can be sent to an external device as a record of the condition of the subject. However, when the alert generator 47 is employed, the alert can be, for example, a tactile signal (e.g., vibration of the mobile device), an audio signal or a visual signal. In some examples, the alert generator 47 can send a signal through the I/O unit 44 to the wearable device 12 to generate the alert. The wearable device 12 can generate a tactile alert (e.g., vibration of the wearable device 12 or the like) to alert the subject of the clinical parameter. As another example, the alert generator 47 can provide a series of alerts of increasing urgency. An initial alert can include a tactile signal. After a predefined time period, if the subject does not respond to the tactile signal (e.g., does not take corrective steps to eliminate the detected risk based on the clinical parameter), the alert generator 47 can generate a visual signal or an audio signal. The alert generator 47 can further escalate the alert generated if the subject still does not respond (e.g., triggering the mobile computing device 14 to alert a supervisor or an emergency response professional of the alert condition).

The alert generator 47 can generate the alert when the clinical parameter satisfies the alert condition. The alert condition can be based, for example, one a comparison of the clinical parameter to a threshold and generate the alert when the clinical parameter is greater than or equal to the threshold. The threshold can be set for the individual subject, standardized for a small group of subjects with the same disease condition or standardized for a large population of subjects with different disease conditions (e.g., for an industry or workplace environment). As an example, the alert generator 47 can determine that the clinical parameter corresponds to a risk of a STF event based on a STF threshold. Based on the detection of the risk of the STF event, the alert generator 47 can generate a just-in-time alert to prevent the occurrence of the STF event. The just-in-time alert can occur immediately before the occurrence of the STF event to prevent the STF event from occurring.

Figure 5:
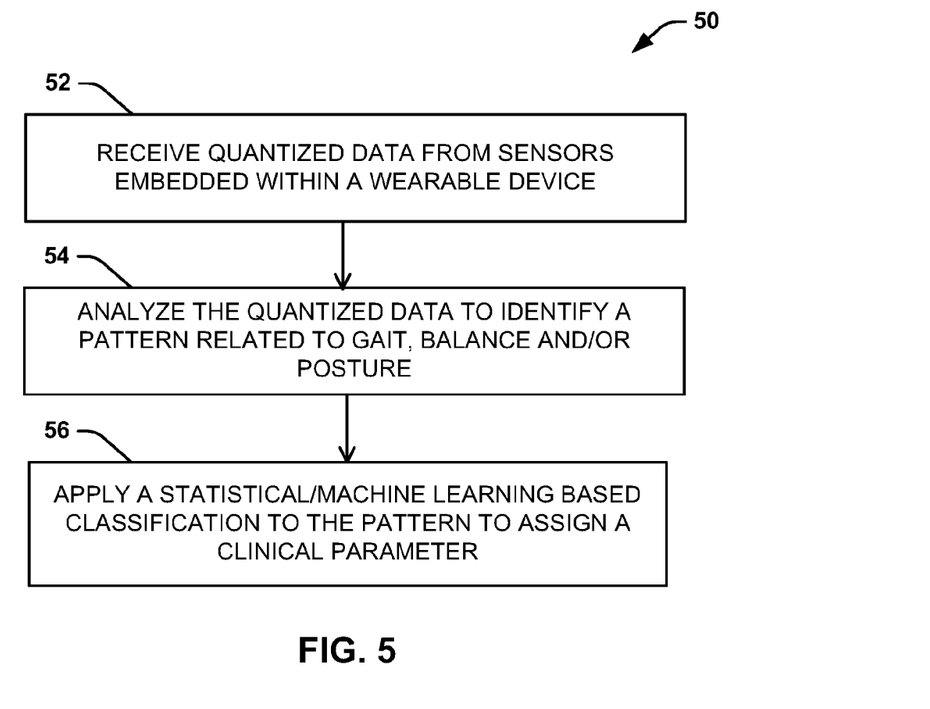
FIG. 5 illustrates an example of a method for analyzing gait, balance or posture information extracted from data collected by one or more wearable devices.
Figure 6:
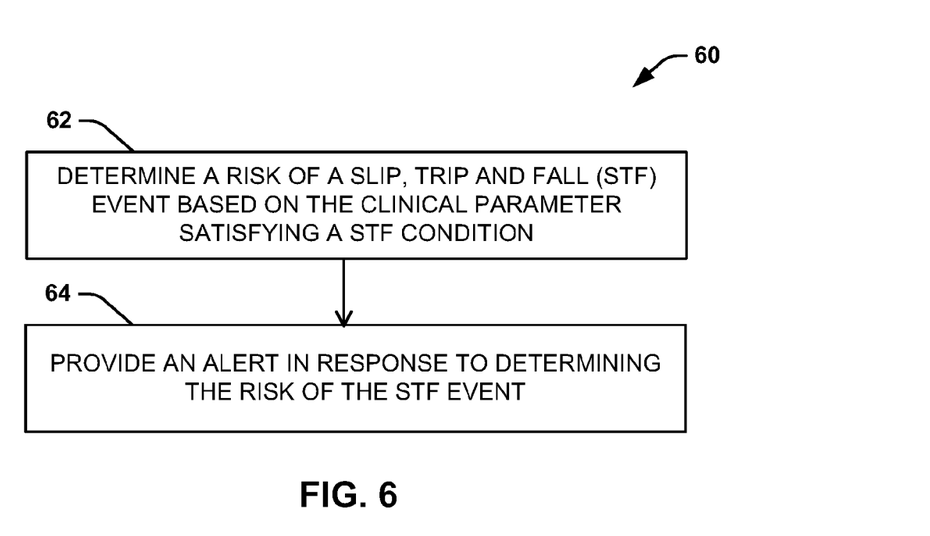
FIG. 6 illustrates an example of a method for preventing a slip, trip and fall (STF) event.

In view of the foregoing structural and functional features described above, example methods that can be performed by the system 10 will be better appreciated with reference to FIGS. 5-6. While, for the purposes of simplicity of explanation, the example methods of FIGS. 5-6 are shown and described as executing serially, the present examples are not limited by the illustrated order, as some actions could in other examples occur in different orders or concurrently from that shown and described herein. Moreover, it is not necessary that all described actions be performed to implement a method. The method can be stored in one or more non-transitory computer-readable media and executed by one or more processing resources, such as described herein.

FIG. 5 illustrates an example of a method 50 that for analyzing gait, balance or posture information extracted from data collected by one or more wearable devices (e.g., wearable device 12). For example, method 50 can be executed by at least a portion of a system (e.g., the mobile computing device 14 shown in FIG. 1) that can include a non-transitory memory that can include a non-transitory memory that stores machine executable instructions and a processing resource to access the non-transitory memory and execute the instructions to cause a computing device to perform the acts of method 50.

At 52, quantized data from sensors embedded within a wearable device (e.g., wearable device 12) can be received (e.g., by mobile computing device 14). In some examples, however, the sensor data received by the mobile computing device 14 is not quantized, and the quantization is done within the mobile computing device 14. One example of the wearable device can include an insole for a shoe 22, as shown in FIG. 2. Other examples can include an entire shoe or a portion of the shoe, such as the bottom. At 54, the quantized data can be analyzed (e.g., by the mobile computing device 14) to identify a pattern related to gait, balance or posture. For example, the pattern can be an unstable pattern or a pattern known to be relevant to gait, balance or posture. At 56, a statistical or machine learning-based classification can be applied (e.g., by the mobile computing device 14 or by an external computing device) to the pattern to assess a clinical parameter. For example, the statistical or machine learning-based classification can compare the pattern to a historical pattern (e.g., a baseline for the subject, a baseline for a group of subjects with the same medical condition or a baseline for a population with different medical conditions).

FIG. 6 illustrates an example of a method 60 for preventing a slip, trip and fall (STF) event. The method 60 can be an extension of method 50, in some examples. At 62, a risk of a STF event can be determined based on the clinical parameter satisfying a STF condition. For example, the STF condition can be a threshold that can be established for the subject, for a group of subjects suffering from the same medical condition or for a population of subjects suffering from different medical conditions. At 64, an alert can be provided (e.g., by the wearable device 12 or by the mobile computing device 14) in response to determining the risk of the STF event. The alert can be a tactile signal, an audio signal or a visual signal.

EXAMPLE

This example shows the wireless portable gait system 10 applied to study human balance (referred to as the "Wearable Gait Lab"). The research was approved by the Case Western Reserve University Institutional Review Board (IRB), under Protocol Numbers IRB-2016-1419 and IRB-2016-1504.

Wearable Gait Lab Implementation

Figure 7:
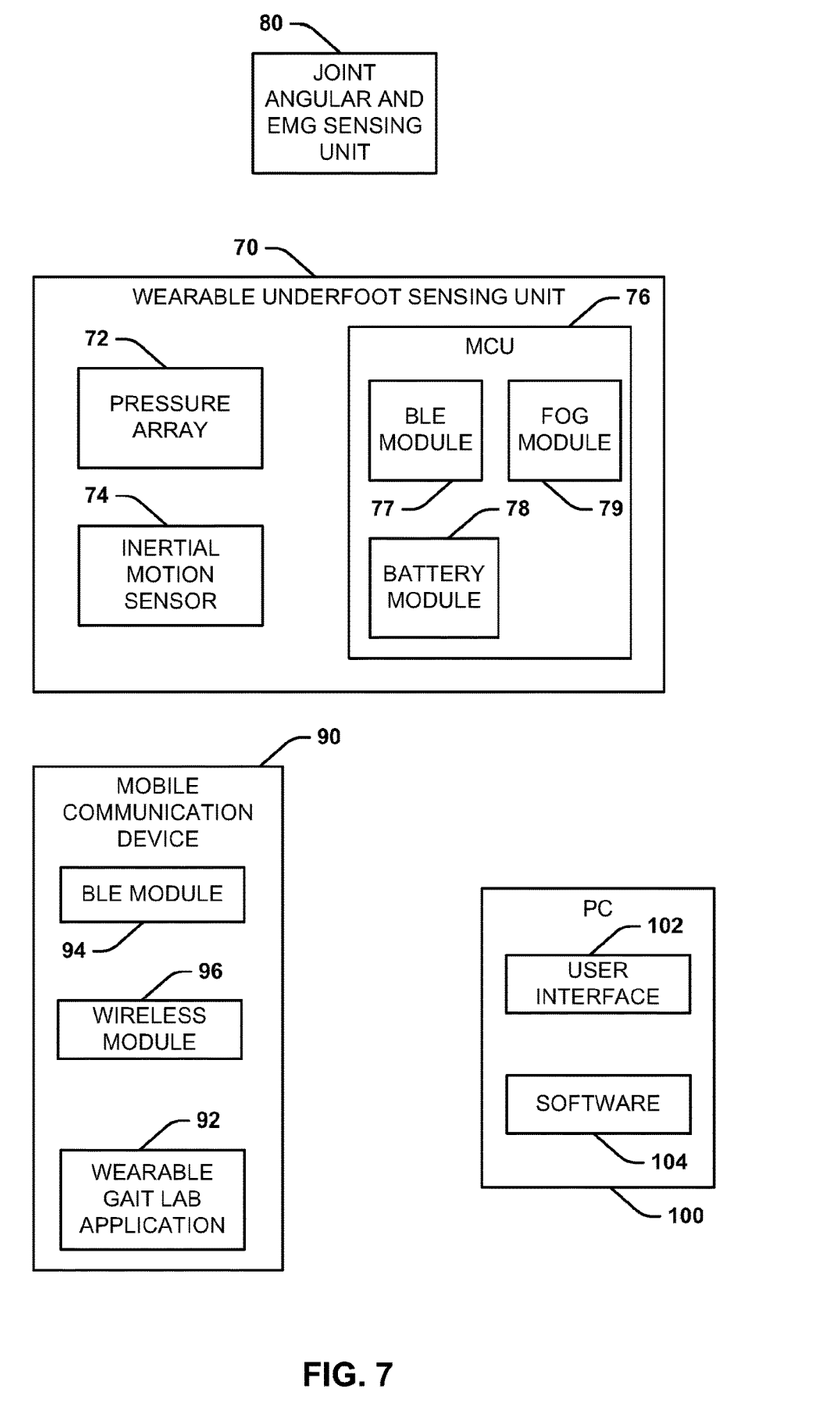
FIG. 7 illustrates an example of the hardware and software used to implement the Wearable Gait Lab example of the wireless portable gait system of FIG. 1.

The hardware and software used to implement the Wearable Gait Lab are discussed in this section and illustrated in FIG. 7.

Wearable Underfoot Force Sensing Unit

The Wearable Underfoot Force Sensing Unit 70 was embodied within shoe insoles. The shoe insoles were placed under subjects' feet and functioned to record plantar pressure data and feet movement data. Each insole in the unit contained a textile pressure array 72, a 9-axis inertial motion sensor 74, a micro control unit (MCU) 76 with a Bluetooth Low Energy (BLE) module 77, a battery module 78, and an on-board Fog computing module 79. The textile pressure array 72 contained forty-eight pressure sensors used to obtain a high resolution plantar pressure map. The 9-axis inertial motion sensor 74 recorded accelerometer, gyroscope and magnetometer data, each in three dimensions, with the X, Y and Z axes of all three parameters sampled. While the accelerometer and the gyroscope measured movement, the magnetometer provided aids for data calibration. The MCU 76 with the Bluetooth Low Energy module 77 provided a wireless channel to connect the insole to a smart electronic device. The battery module 78 contained a battery and a micro USB battery connector, allowing the user to recharge the battery when the insole was out of power.

Joint Angular and EMG Sensing Unit

The Joint Angular and EMG Sensing Unit 80 contained a pair of Myo limb bands (manufactured by the Thalmic Labs of Kitchener, Ontario, Canada) worn on the legs to record IMU and EMG data (eight EMG data are recorded at each timestamp and correlated with the X, Y, Z accelerometer and gyroscope data). The leg IMU and EMG data are recorded concurrently with the data from the Wearable Underfoot Force Sensing Unit 70 in a balance test for future data analysis. Studies have shown that distal (leg and thigh) muscle activities are important indicators of balance adjustment behaviors. The leg EMG data fills the gap in current sensory balance tests so that the test results were more reliable with additional muscle activity indicators.

Since the official Myo SDK for Windows does not provide the option to record both IMU and EMG data from both Myo limb bands in the Joint Angular and EMG Sensing Unit simultaneously, a solution to fulfill data recording purposes was developed so that a CSV data file would be generated for each Myo to record sensory data in the order of timestamp, gyroscope data, accelerometer data orientation data and EMG data. Since EMG data are generated with a higher frequency than IMU data, empty IMU data lines are filled with existing IMU data from the previous timestamp to make the generated data a complete matrix for ease of data analysis. The Myo Dual Data Collector program is used in the data collection process only as a supplement to the application and is the second choice for Myo data recording due to portability.

Wearable Gait Lab Application

The Wearable Gait Lab application 92 was implemented on a mobile computing device 90 (e.g., an Android smartphone) for the purposes of displaying and recording the sensor data from the left, right or both of the lower limbs by bridging the data to xPC host-target system through BLE 94. The application 92 uses a single pane structure in which all functionalities are found by simple scrolling actions. The data types that were recorded are feet accelerometer, feet gyroscope, feet magnetometer, feet pressure, leg accelerometer, leg gyroscope, leg orientation and leg electromyography. The top of the application interface locates the control panel, containing the device information including timestamp, RSSI, connectivity and battery. In the control panel, the user initializes data collection process and uploads recorded data to the cloud server (from the Case School of Engineering Information Technology Department). Under the control panel, the interface contains line charts to plot IMU (accelerometer, gyroscope and magnetometer) and electromyography data in real time and a plantar pressure map to visualize pressure map under each foot.

JavaFX PC User Interface

The JavaFX program is a user interface 102 on a PC 100 for ease of display and analysis of the data collected from the Wearable Gait Lab system. The software 104 was designed for researchers or clinicians to read CSV data generated from the Wearable Gait Lab application and display sensor information same as the Android application. Correspondingly, the software was optimized to share a similar interface style and include charts and graphs in a similar structure of sections for operation affinities while switching between the PC software and the Android application. In the Wearable Gait Lab system, both of the Wearable Gait Lab units are calibrated and the mobile communication device 90 with the application 92 is able to receive the corresponding real-time movement and pressure sensor data and process the data into CSV files. The user interface 102 of the PC software 104 was built with JavaFX, whereas the control functions are contained in controller functions written in Java and the interface was written in FXML and optimized with CSS.

The JavaFX PC user interface 102 read in CSV data exported from the Android user application from the cloud server or the local disk. The CSV data contained information of foot side, the timestamp, nine IMU sensor data including three each from accelerometer, gyroscope and magnetometer and forty-eight pressure sensor data on the Wearable Gait Lab. Similar to the application 90, the PC user interface 102 can be chosen to display underfoot force sensing data information from the left insole, the right insole, both or neither. The PC user interface 102 displays the data in four line charts and one 2D plantar pressure map. The interface 102 would read in the file and display the data in a chronological order in a continuous video form, meaning that it displays the data in the first line of the data as the user imports the file and data in the following lines correspondingly until the last line. Clinicians were also able to adjust the speed of playing, pause the data display process and manually choose display time and save screenshots for future record.

Dynamic Time Warping Algorithm

In some instances, the Wearable Gait Lab system might collect data at a slightly different frequency. In order to find a more accurate time series, the Dynamic Time Warping algorithm (DTW) was implemented to map right and left Wearable Gait Lab's data. Known as a delicate technique to perform an optimal alignment and discern for connections between two time-dependent sequences of different lengths, the Dynamic Time Warping technique is able to support building traceable patterns between right and left insole sensor data, even if the timestamps do not match. During the computing process, a warping path is defined to be the alignment between the two sequences by assigning elements in one sequence to the elements in the other. The warping path is constructed by the following equations of $W_k$, $$W_k = (i,j); \text{ and}$$

$$W_{k+1} = (i',j'); i \leq i' \leq i+1, j \leq j' \leq j+1,$$

where i and j are indexes found in left and right Wearable Gait Lab data. The data collected by sensors at the centers of both lower limbs are used for mapping. The distance of the wrapping path can be calculated by:

$$Dist(W) = \sum_{k=1}^{k=K} [Dist(w_{ki}, w_{kj}),$$

where Dist(W) is the distance of the wrapping path W and Dist(wki;wkj) is the kth element's distance between two data indexes of the wrapping paths.

Example Results

To evaluate the reliability of the Wearable Gait Lab system, existing balance systems, including NeuroCom SMART Balance Master (SBM) and Balance Master (BM) were used as references. Three standard balance tests using Balance Master Systems were applied: 1) Limits of Stability (LOS); 2) Unilateral Stance (US); and 3) Sit-To-Stance (STS). The following Table 1 listed all parameters calculated in each experiments, including center of gravity (COG), sway velocity (SV), reaction time, left/right sway velocity differences (L/R SV difference), weight transfer time (Wt time) and left/right weight transfer symmetry(L/R Wt symmetry). A 24-year-old healthy female with normal conditions participated in these three experiments as a test subject. Since these three experiments did not involve joint motions, data collected by joint angular and EMG sensing unit were not evaluated.

TABLE 1

Experiments and calculated parameters

| | | | |
|---|---|---|---|
| Exp 1 LOS | COG | SV | reaction time |
| Exp 2 US | SV | L/R SV difference | |
| Exp 3 STS | Wt time | SV | L/R Wt symmetry |

Limits of Stability (LOS)

The Limits of Stability (LOS) test is a dynamic balance test aimed to analyze the ability to stay balanced at the maximum distance one can displace Center Of Gravity (COG). The participant was required to stand on a SMART Balance Master (SBM) and wear the Portable Gait Lab systems. Based on the instructions shown on the screen, after hearing a tone, the test subject was commanded to shift his/her center of gravity to one of the eight cardinal and diagonal directions without lifting his/her heels and toes. The two conditions of the LOS experiment include (1) moving COG from the standing phase to the front and (2) moving COG from the standing phase to back.

Linear relations were found between the pressure data collected by sensors in the Portable Gait Lab system and COG given by the SBM. The majority of the cases fit in the linear relation well and the outliers are relatively sparse compared to the data fitted to the relation. The coefficient of determination R2 of the x-axis is 0.9686 and R2 of the y-axis is 0.9508. The p-values of the x-axis and y-axis were both 0.0000≤0.05. Therefore, statistically linear correlations hold.

Each pressure sensor data was multiplied by its weight to compute the COG. The sway velocity at each direction was also calculated based on COG to illustrate how fast one can change their COG in the test environment. A bigger value in sway velocity means a faster speed (a shorter time) one can react to keep balance. The sway velocities can be calculated by:

$$\text{Sway Velocity} = \arcsin\left(\frac{\theta_i - \theta_{i-1}}{t}\right),$$

where $$\theta_i = \arcsin\left(\frac{\text{abs}(COG_i - COG_{i-1})}{\text{height} \times 55\%}\right),$$

where θ is the angle between the human body and the vertical direction orthogonal to the ground. The results are shown in Table 2.

TABLE 2

Sway velocities in LOS experiments.

| | Condition # | | | |
|---|---|---|---|---|
| | LOS 1 | LOS 2 | LOS 3 | LOS 4 |
| Sway Velocity (deg/sec) | 0.81 | 4.61 | 2.80 | 2.28 |

| | Condition # | | | |
|---|---|---|---|---|
| | LOS 5 | LOS 6 | LOS 7 | LOS 8 |
| Sway Velocity (deg/sec) | 0.81 | 2.44 | 2.33 | 1.22 |

Unilateral Stance (US)

The Unilateral Stance (US) test is one of the most common static balance tests used in balance evaluation. The US test measures the postural sway velocities of the test subject when he/she stands on the left or the right foot with eyes open or closed. The test subject wore the Portable Gait Lab system and stood on the NeuroCom SMART Balance Master (SBM). The test subject was asked to lift one foot and try to keep balance with eyes open (EO) and eyes closed (EC) each for 10 seconds. This procedure was repeated three times under each set of conditions. During this test, a harness set was required due to safety concerns.

Both COG and sway velocities are calculated using the same equations mentioned in section 5.1. When the test subject does not maintain balance for 10 seconds, then the sway velocity is set to 12 deg/sec. Table 3 shows the sway velocity results of each condition.

TABLE 3

Sway velocities in Unilateral Stance Tests

| Conditions | Trial 1 | Trial 2 | Trial 3 | Mean |
|---|---|---|---|---|
| Left - Eyes Open | 0.75 | 0.37 | 0.34 | 0.49 |
| Left - Eyes Closed | 0.89 | 1.40 | 1.25 | 1.18 |
| Right - Eyes Open | 1.00 | 0.92 | 0.92 | 0.95 |
| Right - Eyes Closed | 12 | 1.5 | 12 | 8.5 |

As shown in Table 3, the test subject failed to keep balance at Trial 1 and Trial 4 under Condition Right-EC, whereas the sway velocities were measured to be enormously large compared to normal values under other conditions. When the test subject opened eyes, the mean sway velocity on left foot was 0.49 deg/sec and that on the right foot is 0.95 deg/sec. The difference between left and right foot standing with eye open is about 36%. When the test subject closed eyes, the mean sway velocity on the left foot was 1.18 deg/sec and on the right foot was 8.5 deg/sec.

Sit-to-Stance (STS)

The Sit-To-Stance (STS) test is a dynamic balance test designed to quantify the test subject's balance when standing from seated posture. Key parameters measured during the test include weight transfer time, sway velocity during the rising phase and left/right symmetry of the rising force. During the test, the test subject wore the Portable Gait Lab system and sat on a wooden stool placed on Balance Master (BM). The participant was requested to stand up as soon as possible after hearing an alert tone. This procedure was repeated three times. During this test, the harness set was not required.

The results are shown in the Table 4. The mean weight transfer was 0.9 seconds, while the mean sway velocity was 2 deg/sec. On average, the test subject put 30% more weight on his/her right foot.

TABLE 4

Statistical data in Sit-to-Stance tests

| Trial | Weight Transfer Time (sec) | Sway Velocity (deg/sec) | % L/R Wt Symmetry |
|---|---|---|---|
| 1 | 1.0 | 2.06 | 45 |
| 2 | 0.8 | 1.93 | 21 |
| 3 | 0.9 | 2.02 | 23 |
| Mean | 0.9 | 2.00 | 30 |

What has been described above includes example implementations. It is, of course, not possible to describe every conceivable combination of components or methodologies for purposes of describing the present invention, but one of ordinary skill in the art will recognize that many further combinations and permutations are possible. Accordingly, the present invention is intended to embrace all such alterations, modifications and variations that fall within the spirit and scope of the appended claims.

Where the specification or claims recite "a," "an," "a first," or "another" element or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A non-transitory computer readable medium comprising computer executable instructions that when executed by a processor facilitate the performance of operations, the operations comprising:
   receiving sensor data from sensors embedded within an insole device for a shoe, wherein the sensors comprise a three-axis accelerometer, a three-axis gyroscope and an array of pressure sensors;
   analyzing the sensor data to identify a pattern related to gait, balance or posture within the sensor data;
   applying a statistical or machine learning-based classification to the pattern related to gait, balance or posture to assign a clinical parameter to the pattern characterizing a risk of a slip, trip and fall (STF) event; and
   providing an alert in response to determining that the risk of the STF event exceeds a threshold value for the STF event.

2. The non-transitory computer readable medium of claim 1, wherein the data is received according to a short range communication protocol.

3. The non-transitory computer readable medium of claim 2, wherein the short range communication protocol comprises one of a Bluetooth communication protocol, a Bluetooth Low Energy communication protocol and a WiFi communication protocol.

4. The non-transitory computer readable medium of claim 1, wherein the statistical or machine learning-based classification comprises a pattern recognition algorithm that matches the pattern related to gait, balance or posture to a known pattern related to the clinical parameter.

5. The non-transitory computer readable medium of claim 1, wherein the operations further comprise:

analyzing the sensor data to identify another pattern related to gait, balance or posture within the quantized data; and applying the statistical or machine learning-based classification to the other pattern related to gait, balance or posture to assign a clinical parameter to the pattern representing a diagnostic.

6. A system comprising:
an insole device for a shoe comprising:
- a plurality of sensors to detect data;
- a power management unit to set a sampling rate for the plurality of sensors; and
- a data exchange unit to stream a signal comprising the data to a mobile computing device according to a short range communication protocol and to receive data from the mobile computing device; and the mobile computing device comprising:
- an input/output unit to receive the signal streamed according to the short range communication protocol;
- a non-transitory memory storing machine readable instructions; and
- a processing resource to execute the machine readable instructions, the machine readable instructions causing the mobile computing device to:
  - analyze the data to identify a pattern related to gait, balance or posture within the data; and
  - apply a statistical or machine learning-based classification to the pattern related to gait, balance or posture to assign a clinical parameter to the pattern, wherein an alert is generated by the mobile device and/or the insole device based on the clinical parameter.

7. The system of claim 6, wherein the sensors comprise a three-axis accelerometer, a three-axis gyroscope, a three-axis magnetometer and an array of pressure sensors.

8. The system of claim 7, wherein the machine readable instructions further cause the mobile computing device to calibrate the three-axis accelerometer and the three-axis gyroscope based on data from the three-axis magnetometer.

9. The system of claim 7, wherein the array of pressure sensors is implemented on a flexible circuit board.

10. The system of claim 6, wherein the wearable device further comprises an analog-to-digital converter to convert the data to the signal transmitted to the mobile computing device.

11. The system of claim 6, wherein the machine readable instructions further causing the mobile computing device to change a sampling rate of the sensors based on signal reconstruction requirements.

12. The system of claim 6, wherein the machine readable instructions further causing the mobile computing device to:
- determine a risk of a slip, trip and fall (STF) event based on the clinical parameter satisfying a STF condition; and
- provide a just-in-time alert in response to determining the risk of the STF event to prevent occurrence of the STF event;

wherein the alert is the just-in-time alert.

13. The system of claim 12, wherein the communications unit provides an indication of the just-in-time alert to the data exchange unit of the wearable device according to the short range communication protocol and
wherein the wearable device provides the perceivable signal in response to the indication of the alert.

14. The system of claim 12, wherein the just-in-time alert comprises a tactile signal,
wherein the machine readable instructions further causing the mobile computing device to provide another alert upon a time period elapsing without detecting a change in position of the mobile computing device indicating motion of the mobile computing device and
wherein the other alert comprises a visual signal or an audio signal.

15. A method comprising:
receiving, by a mobile device comprising a processor, a signal comprising sensor data from sensors according to a short range communication protocol, wherein the sensors comprise a three-axis accelerometer, a three-axis gyroscope and an array of pressure sensors embedded within an insole device for a shoe;

analyzing, by the mobile device, the sensor data to identify a pattern related to gait, balance or posture within the sensor data;

applying, by the mobile device, a statistical or machine learning-based classification to the pattern related to gait, balance or posture to assign a clinical parameter to the pattern;

determining, by the mobile device, a risk of a slip, trip and fall (STF) event based on the clinical parameter satisfying a STF condition; and providing, by the mobile device, an alert in response to determining the risk of the STF event when the clinical parameter satisfies a STF condition.

16. The method of claim 15, wherein the alert comprises a tactile signal, the method further comprising:
providing another alert after a time, wherein the other alert comprises a visual signal or an audio signal.

* * * * *